United States Patent
Sexton et al.

(10) Patent No.: US 7,819,115 B2
(45) Date of Patent: Oct. 26, 2010

(54) INHALERS AND METHODS OF CONTROLLING AIRFLOW IN INHALERS

(75) Inventors: Douglas A. Sexton, La Jolla, CA (US); Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1680 days.

(21) Appl. No.: 10/768,424

(22) Filed: Jan. 30, 2004

(65) Prior Publication Data

US 2005/0166912 A1 Aug. 4, 2005

(51) Int. Cl.
*A61M 11/00* (2006.01)

(52) U.S. Cl. .................................. 128/200.23

(58) Field of Classification Search ............ 128/200.14, 128/200.18, 200.23, 203.15
See application file for complete search history.

(56) References Cited

U.S. PATENT DOCUMENTS

| | | | | |
|---|---|---|---|---|
| 5,278,626 | A | * | 1/1994 | Poole et al. .................... 356/36 |
| 5,363,842 | A | | 11/1994 | Mishelevich et al. |
| 5,364,838 | A | | 11/1994 | Rubsamen et al. |
| 5,611,332 | A | | 3/1997 | Bono |
| 5,630,409 | A | | 5/1997 | Bono et al. |
| 5,672,581 | A | | 9/1997 | Rubsamen et al. |
| 5,743,250 | A | | 4/1998 | Gonda et al. |
| 5,842,468 | A | | 12/1998 | Denyer et al. |
| 5,884,620 | A | | 3/1999 | Gonda et al. |
| 5,894,841 | A | | 4/1999 | Voges |
| 5,915,378 | A | | 6/1999 | Lloyd et al. |
| 5,941,240 | A | | 8/1999 | Gonda et al. |
| 6,039,042 | A | * | 3/2000 | Sladek .................. 128/200.23 |
| 6,062,212 | A | | 5/2000 | Davison et al. |
| 6,125,844 | A | | 10/2000 | Samiotes |
| 6,158,431 | A | | 12/2000 | Poole |
| 6,167,880 | B1 | | 1/2001 | Gonda et al. |
| 6,196,218 | B1 | | 3/2001 | Voges |
| 6,269,810 | B1 | | 8/2001 | Brooker et al. |
| 6,325,475 | B1 | | 12/2001 | Hayes et al. |

(Continued)

FOREIGN PATENT DOCUMENTS

DE 198 38 711 C 1 6/2000

OTHER PUBLICATIONS

Application entitled "Systems and Methods of Estimating Delivering Doses" having U.S. Appl. No. 10/768,895, filed Jan. 30, 2004.

(Continued)

*Primary Examiner*—Justine R Yu
*Assistant Examiner*—Kristen C Matter

(57) ABSTRACT

Inhaler systems and method of use thereof are disclosed. One exemplary inhaler system, among others, includes an inhalation/exhalation structure including an inhalation/exhalation orifice. In addition, the inhaler system includes a medicament supply system having a medicament ejector disposed adjacent the inhalation/exhalation orifice. The medicament supply system controllably ejects medicament droplets from the medicament ejector. Further, the inhaler system includes a flow control system in fluidic communication with the medicament ejector. The flow control system is configured to entrain the medicament droplets and pass the medicament droplets to the inhalation/exhalation orifice when the patient applies an in-breath to the inhalation/exhalation structure. In addition, the flow control system is configured to impede a flow of air from the inhalation/exhalation orifice to the medicament ejector when the patient applies an out-breath into the inhalation/exhalation structure.

24 Claims, 2 Drawing Sheets

U.S. PATENT DOCUMENTS

Figure 1:
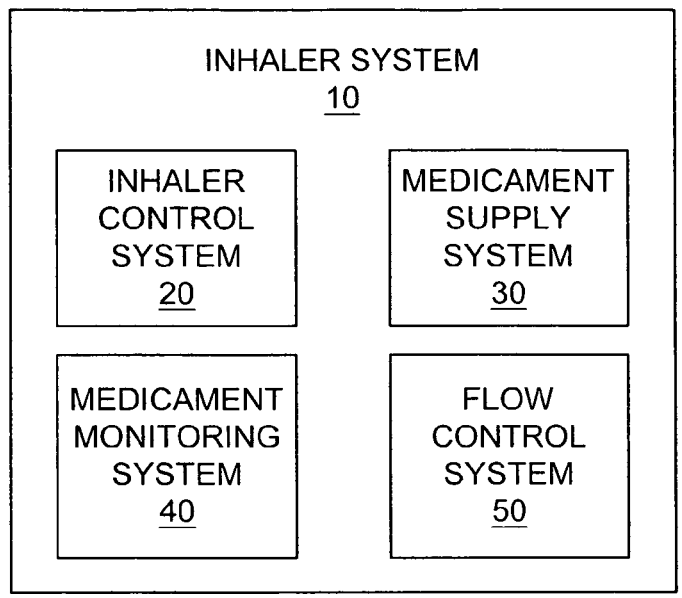

| | | | |
|---|---|---|---|
| 6,390,453 | B1 | 5/2002 | Frederickson et al. |
| 6,443,146 | B1 | 9/2002 | Voges |
| 6,546,927 | B2 | 4/2003 | Litherland et al. |
| 6,598,602 | B1 | 7/2003 | Sjoholm |
| 6,637,430 | B1 | 10/2003 | Voges et al. |
| 6,904,908 | B2 * | 6/2005 | Bruce et al. ............ 128/200.23 |
| 2001/0037806 | A1 | 11/2001 | Scheuch et al. |
| 2002/0026940 | A1 | 3/2002 | Brooker et al. |
| 2002/0065685 | A1 | 5/2002 | Sasaki et al. |
| 2002/0069870 | A1 * | 6/2002 | Farmer ................ 128/200.22 |
| 2002/0071871 | A1 | 6/2002 | Snyder et al. |
| 2002/0092519 | A1 | 7/2002 | Davis |
| 2002/0104531 | A1 * | 8/2002 | Malone ................ 128/203.12 |
| 2002/0195101 | A1 | 12/2002 | Scheuch |
| 2003/0075171 | A1 | 4/2003 | Jones et al. |
| 2003/0101991 | A1 | 6/2003 | Trueba |
| 2003/0145853 | A1 | 8/2003 | Muellner |
| 2003/0172929 | A1 | 9/2003 | Muellner |
| 2003/0200964 | A1 | 10/2003 | Blakely et al. |
| 2005/0039746 | A1 * | 2/2005 | Grychowski et al. ... 128/204.18 |

OTHER PUBLICATIONS

Application entitled "Systems and Methods for Particle Detection" having U.S. Appl. No. 10/768,865, filed Jan. 30, 2004.

* cited by examiner

INHALERS AND METHODS OF CONTROLLING AIRFLOW IN INHALERS

BACKGROUND

There are currently three main methods for medicament delivery via the respiratory tract, namely metered dose inhalers, dry powder inhalers, and nebulizers. Metered dose inhalers ("MDI") are widely used in the management of asthma. The MDI includes a medicament packaged with a propellant in a pressurized aerosol container and can have a valve that releases a volumetric metered dose of aerosol upon actuation. Dry powder inhalers devices rely upon a burst of inspired air to fluidize and draw a dose of an active powder into the bronchial tract. Nebulizers generate an aerosol by atomizing a liquid in a carrier gas stream and require a continuous gas compressor or bulky supply of compressed gas.

Traditionally, inhalers were made of inexpensive components, but recently inhalers are being made of more expensive components such as electronically-controlled medicament drop generators. These new drop generators are expected to have a longer lifetime. However, contamination of the drop generator will present problems to long time use of the inhaler. One example of a way in which the drop generator can be contaminated is through the exhaled breath of the patient. Therefore, there is a need in the industry for an inhaler that overcomes the disadvantages of inhalers with increased lifetime.

SUMMARY

Briefly described, embodiments of this disclosure include inhaler systems and methods of use thereof. One exemplary inhaler system, among others, includes an inhalation/exhalation structure including an inhalation/exhalation orifice. In addition, the inhaler system includes a medicament supply system having a medicament ejector disposed adjacent the inhalation/exhalation orifice. The medicament supply system controllably ejects medicament droplets from the medicament ejector. Further, the inhaler system includes a flow control system in fluidic communication with the medicament ejector. The flow control system is configured to entrain the medicament droplets and pass the medicament droplets to the inhalation/exhalation orifice when the patient applies an in-breath to the inhalation/exhalation structure. In addition, the flow control system is configured to impede a flow of air from the inhalation/exhalation orifice to the medicament ejector when the patient applies an out-breath into the inhalation/exhalation structure.

Another embodiment of the inhaler system, among others, includes an inhalation/exhalation structure including an inhalation/exhalation orifice. In addition, the inhaler system includes a medicament supply system having a medicament ejector disposed adjacent the inhalation/exhalation orifice. The medicament supply system controllably ejects medicament droplets from the medicament ejector. Further, the inhaler system includes a flow control system configured to define at least two different air flow paths. The air flow paths can include an inhalation airflow path and an exhalation airflow path. The inhalation airflow path passes the medicament ejector to entrain the medicament droplets and carry them through the inhalation/exhalation orifice. The exhalation airflow path does not substantially pass through the medicament ejector.

An embodiment of the method of using the inhaler system, among others, includes: providing an inhaler system as described above; carrying the medicament through the inhalation/exhalation orifice with an inhalation airflow flowing through the first inhalation valve; and exhaling into the inhalation/exhalation orifice, wherein the first inhalation valve closes, wherein the exhalation valve opens and an exhalation airflow flows through the exhalation valve and away from the medicament ejector.

BRIEF DESCRIPTION OF THE DRAWINGS

Many aspects of this disclosure can be better understood with reference to the following drawings. The components in the drawings are not necessarily to scale. Moreover, in the drawings, like reference numerals designate corresponding parts throughout the several views.

FIG. 1 illustrates an embodiment of an inhaler system.

FIG. 2 illustrates an embodiment of a breath control valve system incorporated into the inhaler system of FIG. 1.

FIG. 3 illustrates another embodiment of a breath control valve system incorporated into the inhaler system of FIG. 1.

DETAILED DESCRIPTION

Inhaler systems having breath control valve systems are provided. The inhaler system is operated by a patient, in need of a medicament, inhaling and exhaling through the inhaler system. The flow control system controls the flow of the inhaled air across the medicament ejector and substantially prevents the exhaled air from flowing across the medicament ejector by redirecting the flow of the exhaled air. Thus, the inhaler system is adapted to substantially prevent contamination of the medicament ejector, since particles from the exhaled breath are substantially prevented from contacting the medicament ejector.

In general, the inhaler system includes a medicament ejector and a mouthpiece (e.g., an inhalation/exhalation structure) that are coupled by a flow control system. In use, the patient first places their mouth (or nose in some cases) on the mouthpiece and then takes an in-breath or inhales to receive the medicament (e.g., typically in the form of a medicated aerosol). The patient also breathes out or exhales into the mouthpiece during an out-breath.

The medicament ejector includes a face having an array of nozzles or orifice for controllably ejecting medicated aerosol droplets. The medicament ejector is an electronically-controlled drop ejecting device that utilizes a drop generating device (e.g., a thermal bubble generator, a piezo drop generator, and a vibrating porous membrane) to generate droplets of the medicament, which can be entrained in the in-breath.

The flow control system is configured to allow air to entrain the medicament droplets so that they pass to the mouthpiece during an in-breath. In other words, during the in-breath, the flow control system defines an "in-breath airflow path" or "an inhalation airflow" that carries the medicament droplets from the medicament ejector face to the mouthpiece. In addition, the flow control system includes an inlet port for receiving air during an in-breath. During the in-breath of a patient, air flows from the inlet port, past the medicament ejector (entraining the medicament aerosol), and to the mouthpiece along the in-breath airflow path.

The flow control system also defines an "out-breath airflow path" or "exhalation airflow" during the patient's out-breath. The out-breath airflow path does not retrace the in-breath airflow path. By defining two different airflow paths, the flow control system impedes the flow of air from the mouthpiece to the medicament ejector during the out-breath of the patient. Thus, the out-breath airflow path substantially bypasses the medicament ejector to avoid contamination of the medicament ejector during the out-breath. The flow control system also includes an outlet port that is separated physically from the inlet port. During an out-breath of the patient, air flows from the mouthpiece to the outlet port, substantially bypassing the medicament ejector. To provide added assurance that the out-breath air flow path does not substantially impinge upon and contaminate the medicament ejector, one or more valves (e.g., check valves or one-way valves) may be employed that are described in additional detail in the following text and accompanying figures.

FIG. 1 illustrates a block diagram of a representative inhaler system 10 that includes, but is not limited to, an inhaler control system 20, a medicament supply system 30, and a flow control system 50. In addition, the inhaler system 10 can include a medicament monitoring system 40 for monitoring the amount of medicament inhaled and exhaled by the patient.

In general, the inhaler control system 20, the medicament supply system 30, the flow control system 50, and in some instances the medicament monitoring system 40, are communicatively coupled to function together to control the release of the medicament and control the airflow caused by inhalation out of (patient in-breath) and exhalation into (patient out-breath) the inhaler system 10. In practice, the patient inhales on an inhalation/exhalation structure (mouthpiece) of the inhaler system 10 and depresses an actuator (e.g., button or switch) to cause the medicament to be released. As the patient inhales on the inhaler system 10, the flow control system 50 causes inhalation airflow to pass across the medicament ejector. Once the button is activated, the medicament flows with the inhalation airflow into the patient. After inhalation, the patient exhales into the inhaler system 10. At this point, the flow control system 50 redirects the exhalation airflow away from the medicament ejector, which substantially decreases the likelihood of contaminating the medicament ejector. In addition, during the inhalation and exhalation, the medicament monitoring system 40 can be used to monitor the amount of medicament being inhaled by the patient.

The inhaler control system 20 includes, but is not limited to, a computer system and a mechanical system, both of which activate/deactivate the medicament supply system 30. The computer system can include, but is not limited to, programmable logic circuits (e.g., a microprocessor) to control the quantity of medicament released by the medicament supply system 30. The mechanical system can include, but is not limited to, an actuation structure (e.g., button or switch), spring mechanism in communication with the actuation structure, and similar components used to communicate that the patient is requesting medicament release.

The medicament supply system 30 can be activated by the patient depressing the actuation structure in an effort to release the medicament and/or indicate that the patient is ready to receive the medicament. The medicament supply system 30 includes, but is not limited to, a medicament container and a medicament ejector. The inhaler control system 20, in conjunction with the medicament supply system 30, releases a known amount of the medicament from the medicament container and through the medicament ejector. Once the medicament is released, the flow control system 50 uses the inhalation airflow to carry the medicament to the patient during inhalation. During exhalation the flow control system 50 directs the exhalation airflow substantially away from the medicament ejector thereby bypassing the medicament ejector. The flow control system 50 includes, but is not limited to, one or more inhalation/exhalation valves such as a one-way valve (e.g., a valve in which airflow can proceed in one direction or else the valve closes), channels, inlet ports, and outlet ports. The inhalation/exhalation valves control the airflow through the inhaler system 10 by opening and closing under certain pressure conditions during inhalation and exhalation. For example, one inhalation/exhalation valve opens during inhalation while another inhalation/exhalation valve closes. In this instance, the inhalation airflow is controlled by the opening and closing of particular inhalation/exhalation valves. In addition, the opening and/or closing of the inhalation/exhalation valves can be used to activate/deactivate of the medicament supply system 30.

The activation/deactivation of the medicament supply system 30 can be controlled based on information from the medicament monitoring system 40. For example, the medicament monitoring system 40 is adapted to determine if the patient inhaled a threshold amount of the medicament. Based on this determination by the medicament monitoring system 40, the inhaler control system 20 can alert the patient (e.g., an audible and/or visible signal) whether or not the inhalation was successful.

Additional details about the inhaler system 10 can be found in U.S. patent applications entitled "SYSTEMS AND METHODS FOR ESTIMATING DELIVERED DOSES" (HP 200400603) and "SYSTEMS AND METHODS FOR PARTICLE DETECTION" (HP 200400605) having Ser. Nos. 10/768895 and 10/768865 and filed on Jan. 30, 2004, respectively, both of which are incorporated herein by reference.

Figure 2:
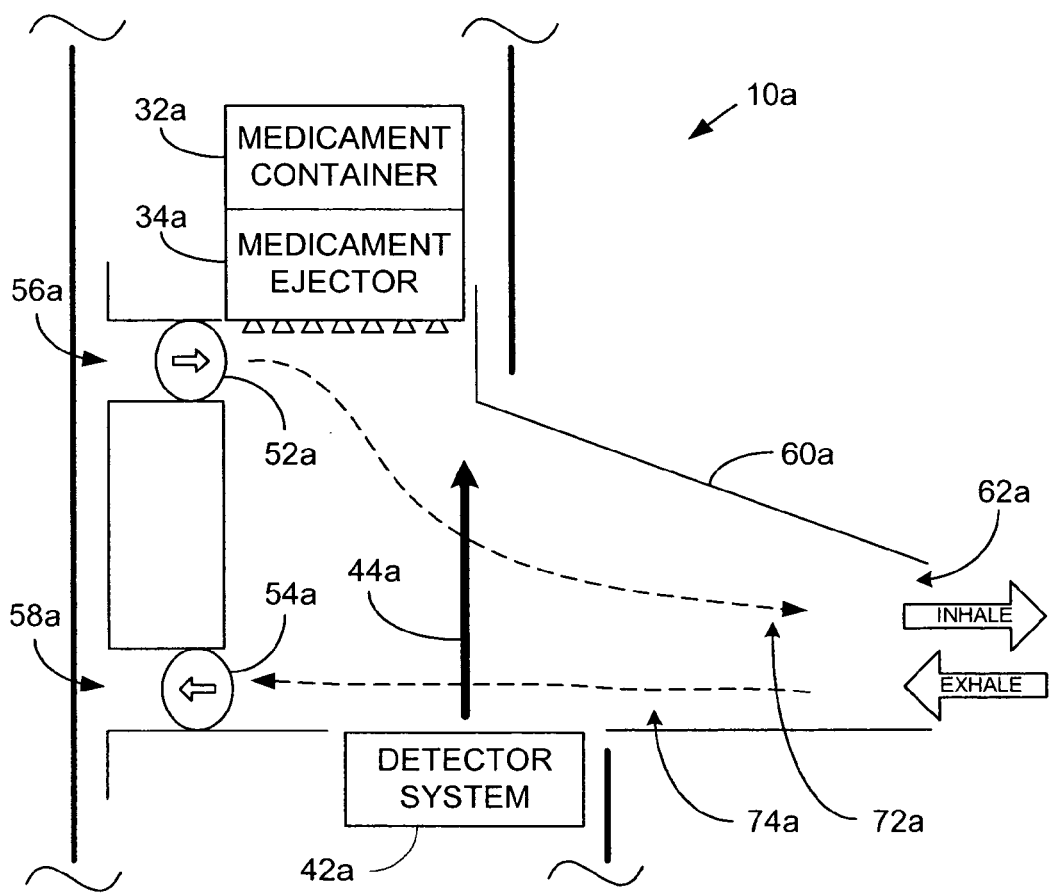
Figure 3:
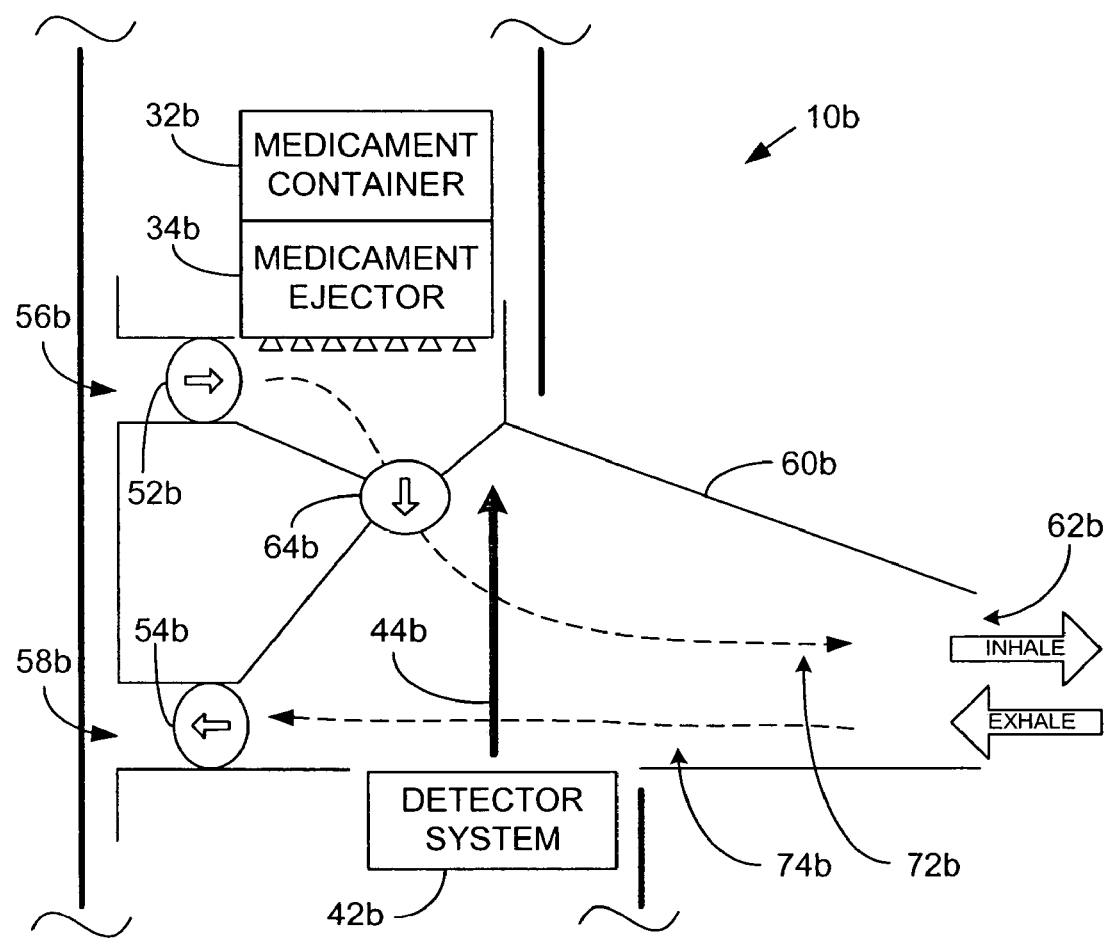

Now having described the inhaler system 10 in general, FIGS. 2 and 3 illustrate exemplary embodiments of the inhaler systems 10a and 10b. These examples are not intended to limit the scope of any embodiment of this disclosure, but rather are intended to provide specific exemplary embodiments. Therefore, one skilled in the art would understand that the components of the inhaler systems 10a and 10b and the configuration of the components within the inhaler systems 10a and 10b can be modified, and it is intended that these modifications be within the scope of the embodiments of this disclosure.

FIG. 2 illustrates a block diagram of a portion of a representative inhaler system 10a. The inhaler system 10a includes a medicament container 32a for housing the medicament and a medicament ejector 34a, which are parts of the medicament supply system 30. The medicament ejector 34a can be, for example, but is not limited to, a piezo electric type device, thermal bubble jet device, or a vibrating porous membrane, to eject the medicament. The various types of medicament containers 32a and the medicament ejectors 34a are known in the art (e.g., U.S. Pat. No. 5,894,841) and are not described in additional detail here.

The inhaler system 10a also includes an inhalation/exhalation structure 60a (e.g., an inhalation/exhalation mouthpiece) having an inhalation/exhalation orifice 62a. The inhalation/exhalation orifice 62a is the point at which the patient contacts the inhaler system 10a to breathe out of and into the inhaler system 10a. The inhalation/exhalation structure 60a can be a permanent part of the inhaler system 10a or it can be a removable and replaceable part of the inhaler system 10a. The inhalation/exhalation structure 60a can have various designs and be made of various materials, all of which are known in the art.

The inhaler system 10a also includes a detection system 42a, which is part of the medicament monitoring system 40. The detection system 42a can be located at various positions within the inhaler system 10a to monitor the medicament flow into and out of the inhaler system 10a. The detection system 42a can include, but is not limited to, at least one laser system and at least one laser detector. In practice, the laser system emits laser light 44*a* during inhalation and exhalation, while the laser detector detects laser light scattered by the medicament passing along the path of the laser light. Additional details about the medicament monitoring system 40 and the detection system 42*a* can be found in U.S. patent applications entitled "SYSTEMS AND METHODS FOR ESTIMATING DELIVERED DOSES" (HP 200400603) and "SYSTEMS AND METHODS FOR PARTICLE DETECTION" (HP 200400605) having Ser. Nos. 10/768895 and 10/768865 and filed on Jan. 30, 2004.

The inhaler system 10*a* also includes a flow control system 50 in fluidic communication with the medicament ejector 34*a*. The flow control system 50 is adapted to control the airflow (inhalation airflow 72*a* and exhalation airflow 74*a*) within the inhaler system 10. In particular, the flow control system 50 causes inhalation airflow 72*a* to pass across the medicament ejector 34. Therefore, as the patient breathes in (e.g., causing the inhalation airflow 72*a* to flow out of the inhaler system 10*a*) and depresses the actuation structure to release the medicament, the inhalation airflow 72*a* carries the medicament through the inhalation/exhalation structure 60*a* and into the patient. After inhalation, the patient exhales into the inhaler system 10*a*. The flow control system 50 redirects the exhalation airflow 74*a* away from the medicament ejector 34*a*, which substantially decreases the likelihood of contaminating the medicament ejector 34*a*.

The flow control system 50 includes, but is not limited to, at least inhalation valve 52*a* and an exhalation valve 54*a*. The inhalation valve 52*a* and an exhalation valve 54*a* can be the same type of valve or different types of valves. The inhalation valve 52*a* and/or the exhalation valve 54*a* can be selected from, but is not limited to, a one-way valve, a check valve, a flapper valve, and combinations thereof.

In addition, the flow control system 50 includes an inlet port 56*a* in fluid communication with the inhalation valve 52*a* and an outlet port 58*a* in fluid communication with the exhalation valve 54*a*. As the patient inhales, the inhalation valve 52*a* opens and air flows through the inlet port 56*a* into the inhaler system 10*a*. As the patient exhales, the exhalation valve 54*a* opens and air flows through the outlet port 58*a* out of the inhaler system 10*a*.

The inhalation valve 52*a* is disposed adjacent the medicament ejector 34*a*, while the exhalation valve 54*a* is disposed away from (e.g., spaced a distance away from) the medicament ejector 34*a*. The position of the inhalation valve 52*a* is selected so that upon the inhalation breath, the inhalation airflow 72*a* passes over the medicament ejector 34*a*. In this manner, the medicament is carried through the inhalation/exhalation structure 60*a* and orifice 62*a* and into the patient. The position of the exhalation valve 54*a* is selected so that upon the exhalation breath, the exhalation airflow 74*a* does not substantially pass over the medicament ejector 34*a*. The inhaler system 10*a* (e.g., positions of the inhalation valve 52*a* and the exhalation valve 54*a*) is desirably configured to limit the contamination of the medicament ejector 34*a*. However, one skilled in the art could design the flow control system 50, the medicament ejector 34*a*, and other components of the inhaler system 10*a* in a different manner than that shown in FIG. 2 to accomplish limiting the contamination of the medicament ejector 34*a*. These additional configurations are contemplated by this disclosure.

In operation, the first inhalation valve 52*a* is only open during inhalation out through the inhalation/exhalation orifice 62*a*, while the exhalation valve 54*a* is closed during inhalation out through the inhalation/exhalation orifice 62*a*. In this manner, the inhalation airflow 72*a* passes over the medicament ejector 34*a*. The first inhalation valve 52*a* is closed during exhalation in through the inhalation/exhalation orifice 62*a*, while the exhalation valve 54*a* is open during exhalation in through the inhalation/exhalation orifice 62*a*. In this manner, the exhalation airflow 74*a* does not substantially contact the medicament ejector 34*a*.

The flow control system 50 can be communicatively coupled with the inhaler control system 20, the medicament supply system 30, and the medicament monitoring system 40 to effectively release the medicament. For example, the patient may depress the actuation structure to release the medicament, but exhale instead of inhale. Since the inhalation valve 52*a* only opens upon inhalation and/or the exhalation valve 54*a* only opens during the exhalation, the flow control system 50 can be configured to communicate with the inhaler control system 20 and/or the medicament supply system 30 when these valves are open and/or closed. Therefore, medicament is not released during patient exhalation.

FIG. 3 illustrates a block diagram of a portion of a representative inhaler system 10*b*. Similar to inhaler system 10*a* in FIG. 2, the inhaler system 10*b* includes a medicament container 32*b* for housing the medicament and a medicament ejector 34*b*, which are parts of the medicament supply system 30. In addition, the inhaler system 10*b* includes an inhalation/exhalation structure 60*b* having an inhalation/exhalation orifice 62*b*. Further, the inhaler system 10*b* includes a detection system 42*b*, which is part of the medicament monitoring system 40.

The inhaler system 10*b* also includes a flow control system 50 in fluidic communication with the medicament ejector 34*b*. The flow control system 50 is adapted to control the airflow (inhalation airflow 72*b* and exhalation airflow 74*b*) within the inhaler system 10*b*. The flow control system 50 includes, but is not limited to, a first inhalation valve 52*b*, a second inhalation valve 64*b*, and an exhalation valve 54*b*. The first inhalation valve 52*b*, the second inhalation valve 56*b*, and the exhalation valve 54*b* can be the same type of valve or different types of valves, as those described in FIG. 2.

In addition, the flow control system 50 includes an inlet port 56*b* in fluid communication with the inhalation valve 52*b* and an outlet port 58*b* in fluid communication with the exhalation valve 54*b*. As the patient inhales, the inhalation valve 52*b* opens and air flows through the inlet port 56*b* into the inhaler system 10*b*. As the patient exhales, the exhalation valve 54*b* opens and air flows through the outlet port 58*a* out of the inhaler system 10*b*.

The first inhalation valve 52*b* and the second inhalation valve 64*b* are disposed adjacent the medicament ejector 34*b*, while the exhalation valve 54*b* is disposed away from the medicament ejector 34*b*. The position of the first inhalation valve 52*b* is selected so that upon the inhalation breath, the inhalation airflow 72*b* passes over the medicament ejector 34*b*. The second inhalation valve 64*b* is disposed between the medicament ejector 34*b* and the inhalation/exhalation orifice 62*b*. In this manner, the medicament is carried through the second inhalation valve 64*b*, through the inhalation/exhalation structure 60*b* and orifice 62*b*, and into the patient.

The position of the exhalation valve 54*b* is selected so that upon the exhalation breath, the exhalation airflow 74*b* does not substantially pass over the medicament ejector 34*b*. In addition, the second inhalation valve 64*b* is positioned to substantially limit contamination of the medicament ejector 34*b*. The inhaler system 10*b* (e.g., positions of the first inhalation valve 52*b*, the second inhalation valve 64*b*, and the exhalation valve 54*b*) is desirably configured to limit the contamination of the medicament ejector 34*b*. However, one skilled in the art could design the flow control system 50, the medicament ejector 34*b*, and other components of the inhaler system 10*b* in a different manner as that shown in FIG. 3 to accomplish limiting the contamination of the medicament ejector 34*b*. These additional configurations are contemplated by this disclosure.

In operation, the first inhalation valve 52*b* and the second inhalation valve 64*b* are only open during inhalation out through the inhalation/exhalation orifice 62*b*, while the exhalation valve 54*b* is closed during inhalation out through the inhalation/exhalation orifice 62*b*. In this manner, the inhalation airflow 72*b* passes over the medicament ejector 34*b* and through the second inhalation valve 64*b*. In other words, upon inhalation by the patient, the second inhalation valve 64*b* opens and then the first inhalation valve opens 52*b*. Once the medicament is ejected, the inhalation airflow 72*b* from the first inhalation valve 52*b* carries the medicament through the second inhalation valve 56*b* and to the patient.

The first inhalation valve 52*b* and the second inhalation valve 64*b* are closed during exhalation in through the inhalation/exhalation orifice 62*b*, while the exhalation valve 54*b* is open during exhalation in through the inhalation/exhalation orifice 62*b*. In this manner, the exhalation airflow 74*b* does not substantially contact the medicament ejector 34*b*. In other words, upon exhalation by the patient, the first and second valves 52*b* and 64*b* close and the exhalation airflow 74*b* is directed through the exhalation valve 54*b* that is open.

In a manner similar to that described above for FIG. 2, the flow control system 50 can be communicatively coupled with the inhaler control system 20, the medicament supply system 30, and the medicament monitoring system 40 to effectively release the medicament.

Many variations and modifications may be made to the above-described embodiments. All such modifications and variations are intended to be included herein within the scope of this disclosure and protected by the following claims.

The invention claimed is:

1. An inhaler system, comprising:
   an inhalation/exhalation structure including an inhalation/exhalation orifice;
   a medicament supply system including a medicament ejector disposed in fluidic communication with the inhalation/exhalation orifice, wherein the medicament supply system controllably ejects medicament droplets from the medicament ejector; and
   a flow control system in fluidic communication with the medicament ejector, the flow control system configured to provide an airflow substantially across a face of the medicament ejector wherein the airflow passes first through an inhalation valve and then across the face of the medicament ejector, wherein the airflow is oriented to entrain the medicament droplets and then pass the medicament droplets to the inhalation/exhalation orifice when a patient applies an in-breath to the inhalation/exhalation structure, and wherein the flow control system is configured to impede a flow of air from the inhalation/exhalation orifice to the medicament ejector when the patient applies an out-breath into the inhalation/exhalation structure.

2. The inhaler system of claim 1, wherein the flow control system comprises a first inhalation valve and an exhalation valve, wherein the first inhalation valve is disposed adjacent the medicament ejector, wherein the first inhalation valve is only open while the patient inhales out through the inhalation/exhalation orifice, wherein the exhalation valve is closed while the patient inhales out through the inhalation/exhalation orifice, wherein the first inhalation valve is closed while the patient exhales in through the inhalation/exhalation orifice, and wherein the exhalation valve is open while the patient exhales in through the inhalation/exhalation orifice.

3. The inhaler system of claim 2, wherein the first inhalation valve and the exhalation valve are each selected from a one-way valve, a flapper valve, a check valve, and combinations thereof.

4. An inhaler system, comprising:

an inhalation/exhalation structure including an inhalation/exhalation orifice;

a medicament supply system including a medicament ejector disposed in fluidic communication with the inhalation/exhalation orifice, wherein the medicament supply system controllably ejects medicament droplets from the medicament ejector;

a flow control system in fluidic communication with the medicament ejector, the flow control system configured to entrain the medicament droplets from a face of the medicament ejector and pass the medicament droplets to the inhalation/exhalation orifice when a patient applies an in-breath to the inhalation/exhalation structure, and wherein the flow control system is configured to impede a flow of air from the inhalation/exhalation orifice to the medicament ejector when the patient applies an out-breath into the inhalation/exhalation structure, the flow control system including:

a first inhalation valve disposed adjacent the medicament ejector, a second inhalation valve disposed between the first inhalation valve and the inhalation/exhalation orifice, and an exhalation valve, wherein the first inhalation valve and the second inhalation valve are only open during inhalation out through the inhalation/exhalation orifice, wherein the exhalation valve is closed while the patient inhales out through the inhalation/exhalation orifice, wherein the first inhalation valve and the second inhalation valve are closed during exhalation in through the inhalation/exhalation orifice, and wherein the exhalation valve is open while the patient exhales in through the inhalation/exhalation orifice.

5. The inhaler system of claim 4, further comprising:

an inlet port in fluidic communication with the first inhalation valve; and an outlet port in fluidic communication with the exhalation valve.

6. The inhaler system of claim 4, wherein the first inhalation valve and the second inhalation valve are each selected from a one-way valve, a flapper valve, a check valve, and combinations thereof.

7. The inhaler system of claim 4, wherein the medicament supply system further comprises at least one medicament.

8. The inhaler system of claim 4, further comprising a medicament monitoring system adapted to monitor the medicament flowing into and out of the inhalation/exhalation orifice during inhalation and exhalation by the patient.

9. The inhaler system of claim 8, wherein the medicament monitoring system comprises a laser system and a laser detector to monitor the medicament.

10. The inhaler system of claim 8, further comprising an inhaler control system adapted to control the medicament monitoring system.

11. The inhaler system of claim 4, wherein the medicament ejector is selected from a thermal bubble generator, a piezo drop generator, and a vibrating porous membrane and combinations thereof.

12. The inhaler system of claim 4, wherein the medicament ejector comprises an array of electronically-activated drop ejectors.

13. The inhaler system of claim 4, wherein the inhalation/exhalation orifice is part of an inhalation/exhalation orifice structure disposed adjacent the medicament supply system and the flow control system.

14. The inhaler system of claim 13, wherein the inhalation/exhalation orifice structure is removable from the inhaler system.

15. A method of dispensing a medicament from an inhaler, comprising:
 providing an inhaler system including
  an inhalation/exhalation orifice;
  a medicament supply system having a medicament ejector disposed adjacent the inhalation/exhalation orifice; and
  a flow control system in fluidic communication with the medicament ejector, wherein the flow control system includes a first inhalation valve and an exhalation valve, wherein the first inhalation valve is disposed adjacent the medicament ejector, wherein the first inhalation valve is only open during inhalation by a patient out through the inhalation/exhalation orifice, wherein the exhalation valve is closed during inhalation out through the inhalation/exhalation orifice, wherein the first inhalation valve is closed during exhalation by the patient in through the inhalation/exhalation orifice, and wherein the exhalation valve is open during exhalation in through the inhalation/exhalation orifice;
 inhaling by the patient through the inhalation/exhalation orifice, wherein the first inhalation valve opens;
 carrying medicament through the inhalation/exhalation orifice with an inhalation airflow flowing first through the first inhalation valve and then across a face of the medicament ejector before reaching the inhalation/exhalation orifice; and
 exhaling by the patient into the inhalation/exhalation orifice, wherein the first inhalation valve closes, wherein the exhalation valve opens and an exhalation airflow flows through the exhalation valve and away from the medicament ejector.

16. A method of dispensing a medicament from an inhaler, comprising:
 providing an inhaler system including
  an inhalation/exhalation orifice;
  a medicament supply system having a medicament ejector disposed adjacent the inhalation/exhalation orifice; and
  a flow control system in fluidic communication with the medicament ejector, wherein the flow control system includes:
   a first inhalation valve disposed adjacent the medicament ejector,
   a second inhalation valve disposed between the first inhalation valve and the inhalation/exhalation orifice, and
   an exhalation valve, wherein the first inhalation valve and the second inhalation valve are only open during inhalation out through the inhalation/exhalation orifice, wherein the exhalation valve is closed during inhalation out through the inhalation/exhalation orifice, wherein the first inhalation valve and the second inhalation valve are closed during exhalation in through the inhalation/exhalation orifice, and wherein the exhalation valve is open during exhalation in through the inhalation/exhalation orifice;
 inhaling by the patient through the inhalation/exhalation orifice, wherein the first inhalation valve opens;
 carrying medicament from a face of the medicament ejector through the inhalation/exhalation orifice with an inhalation airflow flowing through the first inhalation valve; and
 exhaling by the patient into the inhalation/exhalation orifice, wherein the first inhalation valve closes, wherein the exhalation valve opens and an exhalation airflow flows through the exhalation valve and away from the medicament ejector.

17. The method of claim 16, further comprising:
 inhaling through the inhalation/exhalation orifice, wherein the second inhalation valve opens and the first inhalation valve opens;
 carrying the medicament through the second inhalation valve and the inhalation/exhalation orifice with an inhalation airflow flowing through the first inhalation valve and the second inhalation valve; and
 exhaling into the inhalation/exhalation orifice, wherein the second inhalation valve and the first inhalation valve close, wherein the exhalation valve opens and an exhalation airflow flows through the exhalation valve and away from the medicament ejector.

18. The method of claim 16, wherein the provided inhaler supply system further comprises a medicament monitoring system adapted to monitor the medicament flowing into and out of the inhalation/exhalation orifice during inhalation and exhalation.

19. The method of claim 18, further comprising:
 monitoring the medicament flowing out of the inhalation/exhalation orifice during inhalation; and
 monitoring the medicament flowing into the inhalation/exhalation orifice during exhalation.

20. The method of claim 19, further comprising:
 determining the amount of medicament entering the patient.

21. A method of dispensing a medicament from an inhaler, comprising:
 providing an inhaler system including
  an inhalation/exhalation structure including an inhalation/exhalation orifice,
  a medicament supply system having an medicament ejector disposed in fluidic communication with the inhalation/exhalation orifice, wherein the medicament supply system controllably ejects medicament droplets from the medicament ejector, and
  a flow control system in fluidic communication with the medicament ejector;
 inhaling by a patient through the inhalation/exhalation orifice, the flow control system configured to provide an airflow which passes first through an inhalation valve and then across a face of the medicament ejector wherein the airflow is oriented to entrain the medicament droplets in an inhalation airflow and then pass the medicament droplets to the inhalation/exhalation orifice when the patient inhales;
 directing the medicament through the inhalation/exhalation orifice; and
 exhaling by the patient into the inhalation/exhalation orifice, wherein the flow control system is configured to impede an exhalation airflow from the inhalation/exhalation orifice to the medicament ejector when the patient exhales.

22. The method of claim 21, further comprising:

monitoring the medicament flowing out of the inhalation/exhalation orifice during inhalation; and monitoring the medicament flowing into the inhalation/exhalation orifice during exhalation.

23. A method of dispensing a medicament from an inhaler, comprising:

providing an inhaler system including an inhalation/exhalation structure including an inhalation/exhalation orifice;

a medicament supply system having an medicament ejector disposed in fluidic communication with the inhalation/exhalation orifice, wherein the medicament supply system controllably ejects medicament droplets from the medicament ejector; and a flow control system configured to define at least two different air flow paths selected from an inhalation airflow path and an exhalation airflow path;

inhaling by a patient through the inhalation/exhalation orifice;

directing an inhalation airflow along the inhalation airflow path, wherein the inhalation airflow path passes first through an inhalation valve and then across a face of the medicament ejector, entrains the medicament droplets, and then carries them to the inhalation/exhalation orifice;

exhaling by the patient into the inhalation/exhalation orifice; and directing an exhalation airflow along the exhalation airflow path, wherein the exhalation airflow path does not substantially pass the medicament ejector.

24. The method of claim 23, further comprising:

monitoring the medicament flowing out of the inhalation/exhalation orifice during inhalation; and monitoring the medicament flowing into the inhalation/exhalation orifice during exhalation.

* * * * *